US012728166B2

(12) United States Patent
Mann

(10) Patent No.: US 12,728,166 B2
(45) **Date of Patent: *Sep. 8, 2026**

(54) VAGINAL HYDROGEL

(71) Applicant: Brenda K. Mann, Salt Lake City, UT (US)

(72) Inventor: Brenda K. Mann, Salt Lake City, UT (US)

( * ) Notice: Subject to any disclaimer, the term of this patent is extended or adjusted under 35 U.S.C. 154(b) by 254 days.

This patent is subject to a terminal disclaimer.

(21) Appl. No.: 18/418,091

(22) Filed: Jan. 19, 2024

(65) Prior Publication Data

US 2024/0165238 A1 May 23, 2024

Related U.S. Application Data

(63) Continuation of application No. 17/590,213, filed on Feb. 1, 2022, now Pat. No. 11,911,479.

(51) Int. Cl.

| | |
|---|---|
| ***A61K 47/38*** | (2006.01) |
| ***A61K 9/00*** | (2006.01) |
| ***A61K 45/06*** | (2006.01) |
| ***A61K 47/32*** | (2006.01) |
| ***A61K 47/34*** | (2017.01) |
| ***A61P 15/02*** | (2006.01) |
| ***A61P 31/04*** | (2006.01) |
| *A61K 31/565* | (2006.01) |

(52) U.S. Cl.

CPC ............ *A61K 47/38* (2013.01); *A61K 9/0034* (2013.01); *A61K 45/06* (2013.01); *A61K 47/32* (2013.01); *A61K 47/34* (2013.01); *A61P 15/02* (2018.01); *A61P 31/04* (2018.01); *A61K 31/565* (2013.01)

(58) Field of Classification Search

CPC ......... A61K 47/38; A61K 47/32; A61K 47/34

See application file for complete search history.

(56) References Cited

U.S. PATENT DOCUMENTS

| | | | |
|---|---|---|---|
| 8,859,523 | B2 | 10/2014 | Prestwich et al. |
| 2007/0134334 | A1 | 6/2007 | Hahn et al. |
| 2014/0271491 | A1 | 9/2014 | Gittard et al. |
| 2017/0224708 | A1 | 8/2017 | Gravett et al. |
| 2019/0290582 | A1 | 9/2019 | Gerton et al. |
| 2019/0365902 | A1 | 12/2019 | Mann |
| 2021/0169797 | A1 | 6/2021 | Gerton et al. |

OTHER PUBLICATIONS

Almomen et al., Thermosensitive progesterone hydrogel: a safe and effective new formulation for vaginal application. Pharm Res. 2015; 32:2266-79.

Ibrahim et al., Development and characterization of thermosensitive pluronic-based metronidazole in situ gelling formulations for vaginal application. Acta Pharm. 2012; 62:59-70.

Kawarkhe et al., Designing of the mucoadhesive intravaginal spermicidal films. Indian J Pharm Sci. 2010; 72:652-5.

De Araujo Pereira et al., Vaginal mucoadhesive drug delivery systems. Drug Devel Ind Pharm. 2012; 38:643-52.

Chen et al., Evaluation of the efficacy and safety of hyaluronic acid vaginal gel to ease vaginal dryness: A multicenter, Yandomized, controlled, open-label, parallel-group, clinical trial. J Sex Med. 2013; 10:1575-84.

Hiorth et al., Bioadhesive mini-tablets for vaginal drug delivery. Pharmaceutics. 2014; 6:494-511.

Liu et al., Biocompatibility and stability of disulfide-crosslinked hyaluronan films. Biomaterials. 2005; 26:4737-46.

Mather et al., Michael addition reactions in macromolecular design for emerging technologies. Progress in Polymer Science. 2006; 31:487-531.

Nair et al., The thiol-Michael addition click reaction: A powerful and widely used tool in materials chemistry. Chem Mater. 2014; 26:724-44.

Niu et al., Thiol/Acrylate-modified PEO-PPO-PEO triblocks used as reactive and thermosensitive copolymers. Biomacromolecules 2008; 9:2621-2628.

Nowak et al., Preactivated hyaluronic acid: A potential mucoadhesive polymer for vaginal delivery. Intl J Pharm. 2015; 478:383-9.

Valenta et al. The use of mucoadhesive polymers in vaginal delivery. Advanced Drug Delivery Reviews 57 (2005) 1692-1712. (Year: 2005).

Vanderhooft et al., Synthesis and characterization of novel thiol-reactive poly(ethylene glycol) cross-linkers for extracellular-matrix-mimetic biomaterials. Biomacromolecules. 2007; 8:2883-9.

Non-final Office Action dated Apr. 22, 2020 for U.S. Appl. No. 16/233,102.

U.S. Appl. No. 16/233,102; Applicant Initiated Interview Summary dated Jul. 14, 2020.

U.S. Appl. No. 16/233,102; Affidavit-traversing rejections or objections rule 132 dated Jul. 21, 2020.

U.S. Appl. No. 16/233,102; Response of Jul. 21, 2020 to Non-Final Office Action dated Apr. 22, 2020.

U.S. Appl. No. 16/233,102; Applicant Interview Summary dated Jul. 21, 2020.

U.S. Appl. No. 16/233,102; Final Office Action dated Aug. 11, 2020.

U.S. Appl. No. 16/233,102; Examiner Interview Summary dated Oct. 13, 2020.

U.S. Appl. No. 16/233,102; Applicant Initiated Interview Summary dated Oct. 13, 2020.

(Continued)

*Primary Examiner* — Genevieve S Alley

(74) *Attorney, Agent, or Firm* — Laurence & Phillips IP Law

(57) ABSTRACT

The vaginal hydrogel may be a composition which includes a glycosaminoglycan, a reactive molecule, and, in some embodiments, a therapeutic agent. The glycosaminoglycan and the reactive molecule may include either thiol groups or thiol reactive sites and have a pH that is within a range of a normal vaginal environment. Some of the thiol groups may interact with the vaginal mucosa and allow the hydrogel to remain in the vagina for a longer period than existing compounds intended for intravaginal administration. Therapeutic agents may be included in the composition. In these embodiments, the hydrogel acts as a vehicle which delivers the therapeutic agent.

20 Claims, No Drawings

(56) References Cited

OTHER PUBLICATIONS

U.S. Appl. No. 16/233,102; Response of Oct. 28, 2020 to Final Office Action dated Aug. 11, 2020.
U.S. Appl. No. 16/233,102; Terminal Disclaimer dated Oct. 28, 2020.
U.S. Appl. No. 16/233,102; Applicant Interview Summary dated Oct. 28, 2020.
U.S. Appl. No. 16/233,102; Examiner Interview Summary dated Nov. 20, 2020.
U.S. Appl. No. 16/233,102; Notice of Allowance dated Nov. 20, 2020.
U.S. Appl. No. 16/233,102; Examiner Interview Summary dated Jan. 28, 2021.
U.S. Appl. No. 16/233,102; Notice of Allowance dated Feb. 2, 2021.
U.S. Appl. No. 17/179,854; Non-Final Office Action dated Sep. 1, 2022.
U.S. Appl. No. 17/179,854; Response of Dec. 1, 2022 to Non-Final Office Action dated Sep. 1, 2022.
U.S. Appl. No. 17/179,854; Examiner Interview Summary dated Feb. 28, 2023.
U.S. Appl. No. 17/179,854; Notice of Allowance dated Feb. 28, 2023.
U.S. Appl. No. 17/179,854; Notice of Allowance dated Jun. 14, 2023.
U.S. Appl. No. 15/991,870; Non-final Office Action dated May 7, 2020.
U.S. Appl. No. 15/991,870; Response to non-final Office Action dated Aug. 6, 2020.
U.S. Appl. No. 15/991,870; Affidavit-traversing rejections or objections rule 132 of Aug. 6, 2020.
U.S. Appl. No. 15/991,870; Applicant Initiated Interview Summary of Aug. 6, 2020.
U.S. Appl. No. 15/991,870; Applicant Initiated Interview Summary dated Sep. 23, 2020.
U.S. Appl. No. 15/991,870; Final Office Action dated Nov. 9, 2020.
U.S. Appl. No. 15/991,870; Response of Feb. 8, 2021 to Final Office Action dated Nov. 9, 2020.
U.S. Appl. No. 15/991,870; Non-final Office Action dated Mar. 31, 2021.
U.S. Appl. No. 15/991,870; Response of Jun. 30, 2021 to Non-final Office Action dated Mar. 31, 2021.
U.S. Appl. No. 15/991,870; Affidavit-traversing rejections or objections rule 132 of Jun. 30, 2021.
U.S. Appl. No. 15/991,870; Applicant Interview Summary dated Jun. 30, 2021.
U.S. Appl. No. 15/991,870; Examiner Interview Summary dated Jul. 9, 2021.
U.S. Appl. No. 15/991,870; Examiner Interview Summary dated Nov. 2, 2021.
U.S. Appl. No. 15/991,870; Notice of Allowance dated Nov. 2, 2021.
U.S. Appl. No. 15/991,870; Notice of Allowance dated Mar. 14, 2022.
U.S. Appl. No. 15/991,870; Notice of Allowance dated Apr. 26, 2022.
U.S. Appl. No. 15/991,870; Affidavit dated Apr. 29, 2022.
U.S. Appl. No. 17/590,213; Non-final Office Action dated Mar. 2, 2023.
U.S. Appl. No. 17/590,213; Affidavit-traversing rejections or objections rule 132 dated Jun. 2, 2023.
U.S. Appl. No. 17/590,213; Response of Jun. 2, 2023 to Non-final Office Action dated Mar. 2, 2023.
U.S. Appl. No. 17/590,213; Terminal Disclaimer dated Aug. 10, 2023.
U.S. Appl. No. 17/590,213; Examiner Interview Summary dated Aug. 22, 2023.
U.S. Appl. No. 17/590,213; Notice of Allowance dated Aug. 22, 2023.
U.S. Appl. No. 17/590,213; Notice of Allowance dated Oct. 26, 2023.

VAGINAL HYDROGEL

CROSS REFERENCE TO RELATED APPLICATIONS

This application is a continuation application of U.S. patent application Ser. No. 17/590,213 titled "Vaginal Hydrogel" filed Feb. 1, 2022. U.S. patent application Ser. No. 17/590,213 is a continuation application of U.S. patent application Ser. No. 15/991,870 titled "Vaginal Hydrogel" filed May 29, 2018, which claims the benefit of U.S. Provisional Patent Application No. 62/512,588 titled "Vaginal Hydrogel" filed May 30, 2017. Application Ser. Nos. 17/590,213, 15/991,870, 62/512,588 are hereby incorporated by reference in their entirety.

TECHNICAL FIELD

This disclosure relates to vehicles for drug delivery, and more specifically, hydrogels.

BACKGROUND

Vaginitis affects millions of women around the world every year, and bacterial vaginosis is the most common form. Currently, marketed treatments are either intravaginal creams and gels or systemic oral treatments, and the most common drugs are metronidazole, clindamycin, and tinidazole. Metronidazole is currently the most common drug due to the high efficacy of treating harmful bacteria, along with the lack of effect on beneficial lactobacilli. Some of the problems, however, with current treatments include the messiness of intravaginal gels and creams, the potentially lowered efficacy of the drugs in gels and creams as the drug is lost through vaginal secretions, pH imbalances with products that do not have a pH of 3.5-5.0, and for systemic treatments, the problem of introducing the drugs to the entire body, which can produce side effects.

Hydrogels have been utilized as a biomaterial in a variety of medical applications, owing to their high water content, similarity in physical properties to many tissues, and potential for incorporating drugs. These applications include wound healing, tissue engineering and regenerative medicine, drug delivery, and joint lubrication. These hydrogels can be based on natural or synthetic materials, or a combination of the two. Typically, hydrogels will be crosslinked, either through physical interaction—such as simple entanglement, hydrogen bonding, or ionic interaction—or through covalent bonds. Either method of forming hydrogels is typically done at or near what is considered standard physiological pH (i.e., pH 7.4). However, many environments in the body are at a lower pH. In particular, the average pH of the vagina is typically between about 3.2 and 5.0, an environment that favors microflora that are beneficial to the vagina. If the pH of the vagina is increased, a shift in the balance of the microflora occurs, allowing for infection and eventually leading to vaginosis or vaginitis.

Currently available treatments often treat dryness, an infection, or inflammation, but not multiple aspects simultaneously. Additionally, many of these treatments are provided in either a liquid or hydrogel format, but not at a pH that is beneficial for the vaginal environment. Thus, there is a need for a hydrogel that can be delivered vaginally that is at a pH targeted for this environment, namely between about 3.2 and 5.0, and which may provide moisture as well as be used for delivery of therapeutics.

BRIEF SUMMARY OF THE DISCLOSURE

The hydrogels of the present disclosure are particularly useful in treating vaginal dryness, infection, and/or inflammation. These hydrogels may be provided in a composition that includes a glycosaminoglycan which has thiol groups and a molecule that has at least 2 thiol-reactive sites.

The thiol groups and thiol-reactive sites may be in a molar ratio of at least 2:1. The composition may have a pH between about 3.2 and about 5.0. In some embodiments, the glycosaminoglycan is hyaluronic acid or a modified hyaluronic acid. In some embodiments, the molecule is poly(ethylene glycol) diacrylate or poly(ethylene glycol) bisbromoacetate.

In some embodiments, the composition includes a glycosaminoglycan that has thiol-reactive groups and a molecule that has at least 2 thiol groups. In this embodiment, the thiol groups and thiol-reactive groups may be in a molar ratio of at least 2:1 and the composition may have a pH between about 3.2 and about 5.0. In an example, the thiol-reactive sites may be acrylate, methacrylate, bromoacetate, iodoacetate, bromoacetamide, iodoacetamide, or maleimide. In an example, the glycosaminoglycan in this embodiment may be methacrylated or acrylated hyaluronic acid. The molecule in this embodiment may be poly(ethylene glycol) dithiol.

Some embodiments include a mucoadhesive agent. Examples of mucoadhesive agents which may be included in the composition are as follows: methylcellulose, hydroxymethylcellulose, hydroxyethylcellulose, and hydroxypropylcellulose.

The disclosed compositions may be useful to deliver therapeutic agents, including antibacterial agents, antimicrobial agents, antiviral agents, estrogen, estrogen derivatives, and antiinflammatory agents.

DETAILED DESCRIPTION OF THE DISCLOSURE

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

While this invention is susceptible of embodiment in many different forms, there are shown in the provided chemical structures, which will herein be described herein, several specific embodiments with the understanding that the present disclosure is to be considered as an exemplification of the principals of the invention and is not intended to limit the invention to the illustrated embodiments.

The hydrogels described herein may be covalently crosslinked, or both ionically and covalently crosslinked. Covalent crosslinking may be achieved through such means as disulfide crosslinking, Michael-type addition, or photopolymerization. The hydrogel may be based on an anionic polysaccharide, which may be naturally anionic (such as hyaluronic acid or alginate) or may be modified to introduce or increase negative charge, for example, through substitution of hydroxyl groups with carboxyl groups. Particularly suitable are glycosaminoglycans, and a modified hyaluronic acid (hereinafter, "HA"). HA is a natural anionic polysaccharide that is found throughout the body and has been shown to have antiinflammatory properties. Additionally, HA provides moisturization and lubrication.

The hyaluronic acid may be modified to increase the number of negative charges (e.g., carboxymethyl hyaluronic acid) for ionic crosslinking, or to include groups capable of covalent crosslinking. Examples of modifications include the addition of thiol or amine groups, thiol-reactive or amine-reactive groups, or photopolymerizable groups. These photopolymerizable groups may include methacrylate, acrylate, or vinyl groups. In the case of a thiol-modified HA, the hydrogel may be formed by disulfide crosslinking or by combining with a molecule having thiol-reactive groups. In some embodiments, the hyaluronic acid has a thiol modification of about 0.1 to about 1.0 μmol thiol/mg.

Thiol groups on the anionic polysaccharide are useful, as thiol groups may be beneficial for interacting with the vaginal mucosa, allowing the hydrogel to remain in the vagina for an extended period of time. For example, when the hydrogel composition has a thiolated polysaccharide and is combined with a thiol-reactive molecule, the ratio of thiol groups to thiol-reactive groups will be about 2:1 or greater. This can allow for some thiols to be used for covalent crosslinking, while having thiol groups remaining that may be used to interact with the vaginal mucosa.

The hydrogels may be formed at a pH between about 3.2 and 5.0, or may be formed at a higher pH, for example, between about 6.0 and 8.0, and the pH may be lowered once the hydrogel is formed. For forming hydrogels at a pH between about 3.5 and 5.0, particularly appropriate buffers include a lactic acid or citric acid buffer. A lactic acid buffer may be particularly useful for the vaginal environment, as lactic acid/lactate is produced naturally in the vagina. Some types of crosslinking, for example, via Michael-type addition, are typically done at a pH of about 6.5-8.5, as the crosslinking proceeds extremely slowly outside of this range. However, to ensure proper hydrogel formation at lower pH, such as between 3.5 and 5.0, the crosslinking mixture may be placed in a sealed environment for several days until the hydrogel has formed. Additionally, the temperature of the environment may be increased slightly during this time (to about 35-40 degrees C.) to facilitate crosslinking without degrading the polysaccharide.

The resultant hydrogel may be loosely or tightly crosslinked by varying the degree of covalent and/or ionic crosslinking in the hydrogel. This may be accomplished by changing the concentration of the polysaccharide, an additional molecule that reacts with the polysaccharide to form crosslinks, or the number of reactive groups on the polysaccharide or additional molecule. The degree to which the hydrogel is loosely or tightly crosslinked may also be varied by changing the molecular weight of the additional molecule.

A therapeutic agent may be incorporated within the gel, and may be incorporated by mixing, covalently attaching the therapeutic agent to a component of the gel, or through ionic interaction with a component of the gel. For incorporation by mixing, the therapeutic agent may be mixed in either before or after the gel has formed. Therapeutic agents include antimicrobials, including, but not limited to, antibiotics. In some embodiments, therapeutic agents may include antivirals. In other embodiments, the therapeutic agents may include hormones, including but not limited to, estrogen or an estrogen derivative. Still other embodiments may include steroids and anti-inflammatories. Some embodiments may include combinations of therapeutic agents including, but not limited to, those listed as examples herein.

Other components may also be incorporated into the hydrogel to alter physical properties of the resultant hydrogels, enhance mucoadhesion to tissue, or both. Examples of mucoadhesive agents include cellulose derivatives, such as methylcellulose, hydroxymethylcellulose, hydroxyethylcellulose, and hydroxypropylcellulose. The cellulose derivatives may also lead to altered physical properties, such as enhanced viscosity, of the hydrogels.

The hydrogel may include a cationic polymer. In an example, the cationic polymer may be polylysine.

In an embodiment, the composition includes a thiol-modified hyaluronic acid crosslinked to a poly(ethylene glycol) which has thiol-reactive sites. This composition may have a molar ratio of thiol groups to thiol-reactive sites between about 2:1 and about 3:1. The composition may have a pH between about 3.5 and about 4.5.

In an embodiment, the composition includes an anionic polysaccharide that has thiol groups. The composition may further include a cationic polymer and a molecule that has at least 2 thiol-reactive sites. The thiol groups and thiol-reactive sites may be in a molar ratio of at least 2:1. The composition may have a pH between about 3.2 and about 5.0.

In another embodiment, the composition includes an anionic polysaccharide that has thiol groups. The composition may include a cationic polymer and at least a portion of the thiol groups may be disulfide crosslinked. The composition may have a pH between about 3.2 and about 5.0.

In another embodiment, the composition includes comprising an anionic polysaccharide which has photopolymerizable groups. The composition may further include a cationic polymer. In this embodiment, at least a portion of the photopolymerizable groups may be covalently crosslinked. The composition may have a pH between about 3.2 and about 5.0.

In another embodiment, the composition includes an anionic polysaccharide that has thiol-reactive groups. The composition may also include a cationic polymer and a molecule that has at least 2 thiol groups. In this embodiment, the thiol groups and thiol-reactive sites may be in a molar ratio of at least 2:1. The composition may have a pH between about 3.2 and about 5.0.

In another embodiment, the composition includes a glycosaminoglycan which has thiol-reactive groups and a molecule that has at least 2 thiol groups. The thiol-reactive groups and thiol groups may be in a molar ratio of at least 2:1 and the composition may have a pH between about 3.2 and about 5.0.

A therapeutically effective amount of the composition according to the instant disclosure may be provided in a kit for treating vaginosis and/or vaginitis. The kit is within the scope of the instant disclosure.

The instant disclosure also includes a method of treating or preventing vaginosis and/or vaginitis, including the step of administering a therapeutically effective amount of the composition disclosed herein to a subject.

EXAMPLES

The following examples are representative gels that have been formed. Thiol-modified carboxymethyl HA (CMHA-S) was synthesized as described herein. The structure below is the chemical structure of thiol-modified carboxymethyl hyaluronic acid (CMHA-S). For non-modified hyaluronic acid, R=H; for CMHA, R=$CH_2CO_2H$; for CMHA-S, R=$CH_2$—C(O)—NHNH—C(O)—$CH_2CH_2SH$.

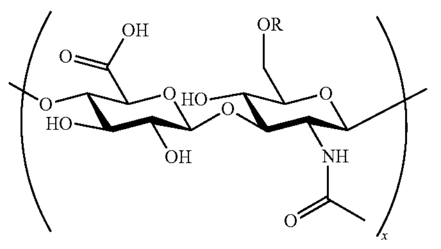

Specifically, medical device-grade HA (900 kDa) was dissolved in 45% NaOH and stirred at room temperature for 2.5 hours. This mixture was then placed in isopropanol, and chloroacetic acid dissolved in isopropanol was added and allowed to react for 1 hour, then settle out of solution for 30 minutes. The liquid was decanted, and the resultant carboxymethyl HA (CMHA) was dissolved in deionized (DI) $H_2O$. The pH was adjusted to 7.0, and the CMHA was purified using tangential flow filtration (TFF).

3,3'-Dithiobis(propanoic dihydrazide) (DTP) was added to the purified CMHA solution and the pH adjusted to 4.75. N-Ethyl-N'-(3-dimethylaminopropyl)carbodiimide (EDAC) was then added and the pH maintained at 4.75 until a gel had formed, which was allowed to react for a total of 4 hours. Dithiothreitol (DTT) was added, the pH adjusted to 8.5 and stirred overnight. The resultant thiolated CMHA (CMHA-S) was purified with TFF.

Poly(ethylene glycol)-bisbromoacetate (PEG-bba) was synthesized as described herein. The structure below is the chemical structure of poly(ethylene glycol)-bisbromoacetate (PEG-bba).

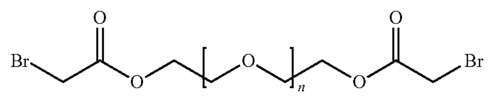

Specifically, 1 mmol dry PEG (3350 Da) was dissolved in anhydrous dichloromethane. Triethylamine (2 mmol) was added, followed by dropwise addition of 4 mmol bromoacetyl chloride under argon. The reaction mixture was left to stir in the dark, under argon, overnight. The product was precipitated in cold diethyl ether, filtered, and dried. The PEG-bba was dissolved in deionized water and purified using dialysis (MWCO 1000), then lyophilized.

Methacrylated HA (MeHA) was synthesized as described herein. The structure below is the chemical structure of methacrylated hyaluronic acid (MeHA). Specifically, MeHA was synthesized by the dropwise addition of methacrylic anhydride (approximately 10-fold excess) to a solution of 1% (w/v) HA (MW=350 kDa) in deionized water adjusted to a pH of 8-9 and reacted on ice for 24 h. The product was precipitated in cold 95% ethanol and filtered. The MeHA was dissolved in deionized water and purified using dialysis, then lyophilized.

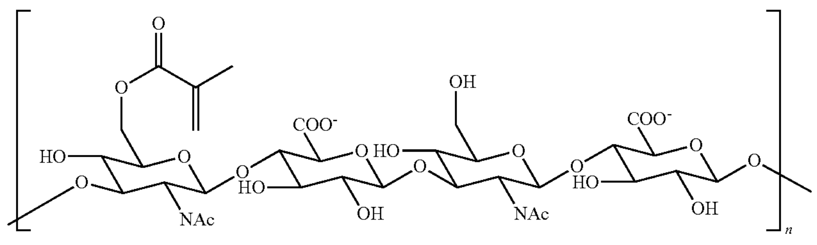

Example 1

A solution of CMHA-S (10 mg/ml) in deionized water was adjusted to a pH of 6.8. A solution of PEG-bba in distilled water (pH 6.8) was added to provide a thiol-to-bromoacetate ratio of 2:1. The mixture was allowed to react for 2 hours. The pH of the resultant loosely crosslinked gel was adjusted to 3.5.

Example 2

A loosely crosslinked gel was prepared as in Example 1, except 1 ml of a polylysine solution (MW 150,000; 10 mg/ml) in deionized water was added per 100 ml of CMHA-S solution and mixed for 30 minutes prior to adding the PEG-bba solution. As in Example 1, this mixture was allowed to react for 2 hours, after which the pH was adjusted to 3.5.

Example 3

A solution of CMHA-S (10 mg/ml) in deionized water was adjusted to a pH of 3.8. A solution of PEG-bba in distilled water (pH 4.0) was added to provide a thiol-tobromoacetate ratio of 2:1. The mixture was allowed to react for 3 days, at which time a loosely crosslinked gel had formed with a pH of 3.9.

Example 4

A loosely crosslinked gel was prepared as in Example 3, except that prior to adding the PEG-bba solution, methylcellulose (14 cPs) was mixed into the CMHA-S solution to provide a final methylcellulose concentration of 5 mg/ml. The pH of the viscous, loosely crosslinked gel was 4.0.

Example 5

MeHA is dissolved in deionized water (pH 4.5) to 15 mg/ml, and polylysine (MW 150,000) is added to induce ionic crosslinking. After 30 minutes of mixing, a photoinitiator (acetophenone in n-vinylpyrrolidone, 3 mg/ml) is added and UV light (365 nm, 10 mW/cm·sup.2) used to photocrosslink and form a gel.

Example 6

A solution of MeHA (15 mg/ml) in deionized water is adjusted to a pH of 6.8. A solution of PEG-dithiol in distilled water (pH 6.8) is added to provide a thiol-to-methacryl ratio of 2:1. The mixture is allowed to react until a gel is formed. The pH of the gel is then adjusted to about 4.0.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

I claim:

1. A method of treating vaginal dryness, infection, and/or inflammation, the method comprising vaginally administering to a subject in need thereof, a crosslinked composition comprising:

a glycosaminoglycan comprising a plurality of thiol groups; and a molecule comprising poly(ethylene glycol), the poly (ethylene glycol) comprising at least two thiol-reactive sites;

wherein the molar ratio of the thiol groups to the thiol-reactive sites is at least 2:1, wherein the composition has a pH between about 3.2 and about 5.0, wherein the glycosaminoglycan crosslinks to the poly (ethylene glycol), and wherein the composition comprises about 0.05 to about 0.2 μmol uncrosslinked thiol groups per mg of the glycosaminoglycan.

2. The method of claim 1, wherein the glycosaminoglycan has a thiol modification of about 0.1 to about 0.4 μmol thiol per mg of glycosaminoglycan.

3. The method of claim 1, wherein the composition has a pH between about 3.2 and about 4.5.

4. The method of claim 1, wherein the glycosaminoglycan comprises modified hyaluronic acid having a thiol modification of about 0.1 to about 0.3 μmol thiol per mg of hyaluronic acid.

5. The method of claim 1, wherein the glycosaminoglycan comprises a thiol-modified hyaluronic acid, wherein the molar ratio of the thiol groups to the thiol-reactive sites is between 2:1 and about 3:1; and wherein the composition has a pH between about 3.5 and about 4.5.

6. The method of claim 1, wherein the composition further comprises a therapeutic agent.

7. The method of claim 6, wherein the therapeutic agent comprises one or more of an antimicrobial agent, an antibacterial agent, an antiviral agent, an antiinflammatory agent, a steroid, an estrogen, and an estrogen derivative.

8. The method of claim 1, wherein the composition further comprises at least one of a cationic polymer, a mucoadhesive agent, or any combination thereof.

9. A method for treating vaginal dryness, infection, and/or inflammation, the method comprising vaginally administering to a subject in need thereof, a crosslinked composition comprising:

an anionic polysaccharide comprising a plurality of thiol groups;

a cationic polymer; and a molecule comprising poly(ethylene glycol), the poly (ethylene glycol) comprising at least two thiol-reactive sites;

wherein the molar ratio of the thiol groups to the thiol-reactive sites is at least 2:1, wherein the composition has a pH between about 3.2 and about 5.0, wherein the anionic polysaccharide crosslinks to the poly (ethylene glycol), and wherein the composition comprises about 0.05 to about 0.2 μmol uncrosslinked thiol groups per mg of the anionic polysaccharide.

10. The method of claim 9, wherein the anionic polysaccharide has a thiol modification of about 0.1 to about 0.4 μmol thiol per mg of polysaccharide.

11. The method of claim 9, wherein the composition has a pH between about 3.2 and about 4.5.

12. The method of claim 9, wherein the anionic polysaccharide comprises a modified hyaluronic acid.

13. The method of claim 9, wherein the anionic polysaccharide comprises a modified glycosaminoglycan.

14. The method of claim 9, wherein the composition further comprises a therapeutic agent.

15. The method of claim 14, wherein the therapeutic agent comprises one or more of an antimicrobial agent, an antibacterial agent, an antiviral agent, an antiinflammatory agent, a steroid, an estrogen, and an estrogen derivative.

16. The method of claim 9, wherein the composition further comprises at least one of a therapeutic agent, a mucoadhesive agent, or any combination thereof.

17. A kit for treating vaginosis and/or vaginitis, the kit comprising:

instructions for use, and a therapeutically effective amount of a crosslinked composition, wherein the crosslinked composition comprises;

a glycosaminoglycan comprising a plurality of thiol groups, and a molecule comprising poly(ethylene glycol), the poly (ethylene glycol) comprising at least two thiol-reactive sites, wherein the molar ratio of the thiol groups to the thiol-reactive sites is at least 2:1, wherein the composition has a pH between about 3.2 and about 5.0, wherein the glycosaminoglycan crosslinks to the poly (ethylene glycol), and wherein the composition comprises about 0.05 to about 0.2 μmol uncrosslinked thiol groups per mg of the glycosaminoglycan.

18. The kit of claim 17, wherein composition has a pH between about 3.2 and about 4.5.

19. The kit of claim 17, wherein the glycosaminoglycan has a thiol modification of about 0.1 to about 0.4 μmol thiol per mg of glycosaminoglycan.

20. The kit of claim 17, wherein the composition further comprises at least one of a cationic polymer, a mucoadhesive agent, a therapeutic agent, or any combination thereof.

* * * * *